US006231613B1

(12) United States Patent
Greff et al.

(10) Patent No.: US 6,231,613 B1
(45) Date of Patent: May 15, 2001

(54) METHODS FOR SOFT TISSUE AUGMENTATION IN MAMMALS

(75) Inventors: Richard J. Greff, St. Pete Beach, FL (US); David E. Silverman, Palo Alto; Alan Stein, Moss Beach, both of CA (US)

(73) Assignee: Enteric Medical Technologies, Inc., Foster City, CA (US)

(*) Notice: Subject to any disclaimer, the term of this patent is extended or adjusted under 35 U.S.C. 154(b) by 0 days.

(21) Appl. No.: 09/210,736

(22) Filed: Dec. 15, 1998

(51) Int. Cl.$^7$ ............................................. A61F 2/36
(52) U.S. Cl. ..................... 623/23.58; 623/902; 604/264
(58) Field of Search ........................... 623/11, 902, 23.58; 604/264; 523/113

(56) References Cited

U.S. PATENT DOCUMENTS

| | | | |
|---|---|---|---|
| 4,631,188 | 12/1986 | Stoy et al. | 424/81 |
| 4,938,763 | 7/1990 | Dun et al. | 604/891.1 |
| 5,368,859 | * 11/1994 | Dunn et al. | 424/426 |
| 5,580,568 | * 12/1996 | Greff et al. | 424/423 |
| 5,667,767 | 9/1997 | Greff et al. | 424/9.411 |
| 5,695,480 | * 12/1997 | Evans et al. | 604/264 |
| 5,755,658 | 5/1998 | Wallace et al. | 600/30 |
| 5,785,642 | 7/1998 | Wallace et al. | 600/30 |

FOREIGN PATENT DOCUMENTS 0 713 707 * 5/1996 (EP) .

OTHER PUBLICATIONS

"Plastic Surgery: The Booming Business of Age Retardation", Med. Data Intl., pp. 278–281, Nov./Dec. 1997.
Costantino, P.D., et al., "Soft–Tissue Augmentation and Replacement in the Head and Neck", Otol. Clin. No. Am., 27(1):1–12, Feb. 1994.
Matton, G., et al., "The History of Injectable Biomaterials and the Biology of Collagen", Aesth. Plast. Surg., 9:133–140, 1985.
Elson, M.L., "Dermal Filler Materials", Derma. Clin., 11(2):361–367, Apr. 1993.
Ford, C.N., et al., "Role of Injectable Collagen in the Treatment of Glottic Insufficiency: A Study of 119 Patients", Ann. Otol. Rhinol. Laryngol., 101: 237–247, 1992.
Remacle, M., et al., "Further Morphologic Studies on Collagen Injected into Canine Vocal Folds", Ann. Otol. Rhinol. Laryngol., 100: 1007–1014, 1991.
Cukier, J., et al., "Association between Bovine Collagen Dermal Implants and a Dermatomyositis or a Polymyositis–like Syndrome", Ann. Intern. Med., 118: 920–928, 1993.
Overholt, M.A., et al., "Granulomatous Reaction to Collagen Implant: Light and Electron Microscopic Observations", Cutis, 51: 95–98, Feb. 1993.
Hanke, C.W., et al., "Abcess formation and local necrosis after treatment with Zyderm or Zyplast Collagen Implant", Amn. Acad. Derm., 2(1): 319–326, Aug. 1991.
Piacquadio, D.J., "Epitomes–Important Advances in Clinical Medicine", Section on Dermatology, Calif. Med. Assn.
Takayama, E., et al., "Is injectable collagen truly safe?", J. Laryngol. Oto., 106: 704–708, Aug. 1992.
Mladick, R.A., "Twelve Months of Experience with Bioplastique", Aesth. Plast. Surg., 16: 69–76, 1992.
Pieyre, J.–M., "Collagen Injections: Two Years' Experience", Aesth. Plast. Surg., 9; 153–154, 1985.
Tolleth, H.., "Long–Term Efficacy of Collagen", Aesth. Plast. Surg., 9: 155–158, 1985.
Nicolle, F.V., "Correction of Age– and Disease–Related Contour Deficiencies of the Face", Aesth. Plast. Surg.., 9: 159–162, 1985.
Jost, G., "Experience with Collagen Injection for the Correction of Contour Deficiencies", Aesth. Plast. Surg., 9: 163–165, 1985.
Ersek, R.A., et al., "Bioplastique: A New Textured Copolymer Microparticle Promises Permanence in Soft–Tissue Augmentation", Plast. Recon. Surg., 87(4): 693–702, Apr. 1991.
Ersek, R.A., et al., "Bioplastique™: A New Biphasic Polymer for Minimally Invasive Injection Implantation", Aesth. Plast. Surg., 16: 59–65, 1992.
Ersek, R.A., "Bioplastique: Specific Technical Advice on Its Use and Possible Complications", Aesth. Plast. Surg., 16: 67–68, 1992.
Simons, G., et al., "Utilization of Injectable Microimplants in Aesthetic Facial Surgery", Aesth. Plast. Surg., 16: 77–82, 1992.
Beisang, A.A. III, et al., "Mammalian Response to Subdermal Implantation of Textured Microimplants", Aesth. Plast. Surg., 16: 83–90, 1992.
Rosen, T., et al., "Use of gelatin matrix implant in patients hypersensitive to bovine collagen", J. Amn. Acad. Dermat., p. 848.
Planas, J., et al., "Twenty Years of Experience with Particulate Silicone in Plastic Surgery", Aesth. Plast. Surg., 16: 53–57, 1992.
Kinugasa, et al., "Direct Thrombosis of Aneurysms with Cellulose Acetate Polymer", J. Neurosurg., 77: 501–507, 1992.

(List continued on next page.)

Primary Examiner—David J. Isabella
Assistant Examiner—Choon P. Koh
(74) Attorney, Agent, or Firm—Flehr Hohbach Test Albritton & Herbert LLP

(57) ABSTRACT

Disclosed are methods for soft tissue augmentation in a mammal wherein a composition comprising a biocompatible polymer having a water equilibrium content of less than about 15% and a biocompatible solvent is delivered to the tissue of the mammal to be augmented.

14 Claims, No Drawings

OTHER PUBLICATIONS

Kinugasa, et al., "Early Treatment of Subarachnoid Hemorrhage After Preventing Rerupture of an Aneurysm", J. Neurosurg., 83: 34–41, 1995.

Kinugasa, et al., "Prophylactic Thrombosis to Prevent New Bleeding and to Delay Aneurysm Surgery", Neurosurg., 36: 661, 1995.

Taki, et al., "Selection and Combination of Various Endovascular Techniques in the Treatment of Giant Aneurysms", J. Neurosurg., 77: 37–42, 1992.

Park, et al., "New Polymers for Therapeutic Embolization", Poster #47, Meeting of Radiological Society of North America, 1993.

* cited by examiner

METHODS FOR SOFT TISSUE AUGMENTATION IN MAMMALS

BACKGROUND OF THE INVENTION

1. Field of the Invention

This invention is directed to methods for soft tissue augmentation in mammals generally and humans in particular. In these methods, a composition comprising a biocompatible polymer and a biocompatible solvent is delivered to the tissue of a mammal.

The biocompatible polymer is selected to be soluble in the biocompatible solvent, but insoluble in the tissue. The biocompatible solvent is miscible or soluble in the fluids of this tissue and, upon contact with such fluids, the biocompatible solvent quickly diffuses away whereupon the biocompatible polymer precipitates to augment the tissue at the delivery site in the mammal.

REFERENCES

The following publications are cited in this application as numbers in brackets ([ ]):

1. "Plastic Surgery: The Booming Business of Age Retardation", *Med. Data Intl., Inc.*, pp. 278–281 (November/December 1997).
2. Costantino, P. D., et al., "Soft-Tissue Augmentation and Replacement in the Head and Neck", *Otol. Clin. No. Am.*, 27(1):1–12 (February 1994).
3. Matton, G., et al., "The History of Injectable Biomaterials and the Biology of Collagen", *Aesth. Plast. Surg.*, 9:133–140 (1985).
4. Elson, M. L., "Dermal Filler Materials", *Derma. Clin.*, 11(2):361–367 (April 1993).
5. Ford, C. N., et al., "Role of Injectable Collagen in the Treatment of Glottic Insufficiency: A Study of 119 Patients", *Ann. Otol. Rhinol. Laryngol.*, 101:237–247 (1992).
6. Remacle, M., et al., "Further Morphologic Studies on Collagen Injected into Canine Vocal Folds", *Ann. Otol. Rhinol. Laryngol.*, 100:1007–1014(1991).
7. Cukier, J., et al., "Association between Bovine Collagen Derral Implants and a Dermatomyositis or a Polymyositis-like Syndrome", *Ann. Intern. Med.*, 118:920–928 (1993).
8. Overholt, M. A., et al., "Granulomatous Reaction to Collagen Implant: Light and Electron Microscopic Observations", *Cutis*, 51:95–98 (February 1993).
9. Hanke, C. W., et al., "Abscess formation and local necrosis after treatment with Zyderm or Zyplast Collagen Implant", *Amn. Acad. Derm.*, 2(1)319–326 (August 1991).
10. Piacquadio, D. J., "Epitomes—Important Advances in Clinical Medicine", Section on Dermatology, *Calif. Med. Assn.*
11. Takayama, E., et al., "Is injectable collagen truly safe?", *J Laryngol. Oto.*, 106:704–708 (August 1992).
12. Mladick, R. A., "Twelve Months of Experience with Bioplastique", *Aesth. Plast. Surg.*, 16:69–76 (1992).
13. Pieyre, J. -M., "Collagen Injections: Two Years' Experience", *Aesth. Plast. Surg.*, 9:153–154 (1985).
14. Tolleth, H., "Long-Term Efficacy of Collagen", *Aesth. Plast. Surg.*, 9:155–158 (1985).
15. Nicolle, F. V., "Correction of Age- and Disease-Related Contour Deficiencies of the Face", *Aesth. Plast. Surg.*, 9:159–162 (1985).
16. Jost, G., "Experience with Collagen Injection for the Correction of Contour Deficiencies", *Aesth. Plast. Surg.*, 9:163–165 (1985).
17. Ersek, R. A., et al., "Bioplastique: A New Textured Copolymer Microparticle Promises Permanence in Soft-Tissue Augmentation", *Plast. Recon. Surg.*, 87(4):693–702 (April 1991).
18. Ersek, R. A., et al., "Bioplastique™: A New Biphasic Polymer for Minimally Invasive Injection Implantation", *Aesth. Plast. Surg.*, 16:59–65 (1992).
19. Ersek, R. A., "Bioplastique: Specific Technical Advice on Its Use and Possible Complications", *Aesth. Plast. Surg.*, 16:67–68 (1992).
20. Simons, G., et al., "Utilization of Injectable Microimplants in Aesthetic Facial Surgery", *Aesth. Plast. Surg.*, 16:77–82 (1992).
21. Beisang, A. A. III, et al., "Mammalian Response to Subdermal Implantation of Textured Microimplants", *Aesth. Plast. Surg.*, 16:83–90 (1992).
22. Rosen T., et al., "Use of gelatin matrix implant in patients hypersensitive to bovine collagen", *J Amn. Acad. Dermat.*, p. 848.
23. Planas, J., et al., "Twenty Years of Experience with Particulate Silicone in Plastic Surgery", *Aesth. Plast. Surg.*, 16:53–57 (1992).
24. Kinugasa, et al., "Direct Thrombosis of Aneurysms with Cellulose Acetate Polymer", *J Neurosurg.*, 77:501–507 (1992).
25. Kinugasa, et al., "Early Treatment of Subarachnoid Hemorrhage After Preventing Rerupture of an Aneurysm", *J Neurosurg.*, 83:34–41 (1995).
26. Kinugasa, et al., "Prophylactic Thrombosis to Prevent New Bleeding and to Delay Aneurysm Surgery", *Neurosurg.*, 36:661 (1995).
27. Greff, et al., U.S. patent Ser. No. 5,580,568 for "Cellulose Diacetate Compositions for Use in Embolizing Blood Vessels", issued Dec. 3, 1996.
28. Greff, et al., U.S. patent Ser. No. 5,667,767 for "Compositions for Use in Embolizing Blood Vessels", issued Sep. 16, 1997.
29. Taki, et al., "Selection and Combination of Various Endovascular Techniques in the Treatment of Giant Aneurysms", *J. Neurosurg.*, 77:37–42 (1992).
30. Park, et al., "New Polymers for Therapeutic Embolization", Poster #47, Meeting of Radiological Society of North America (1993).
31. Stoy, et al., U.S. Pat. No. 4,631,188, "Injectable Physiologically-acceptable Polymeric Composition", issued Dec. 23, 1986.
32. Dunn, et al., U.S. Pat. No. 4,938,763, "Biodegradable In-Situ Forming Inplants and Methods of Producing the Same", issued Jul. 3, 1990.

The disclosure of each of the above publications is herein incorporated by reference in its entirety to the same extent as if each individual publication was specifically and individually indicated to be incorporated herein by reference in its entirety.

2. State of the Art

Soft tissue augmentation to correct defects and counteract the effects of aging is becoming increasingly important. Currently, soft tissue augmentation may be achieved by the use of such means as injectable collagen, fat injections, silicone injections, insertion of shaped polyethylene based plugs, insertion of hollow-shaped tubes composed of expanded polytetrafluoroethylene or the injection of hydrogel based polymer compositions [1,31].

The ideal material for soft tissue augmentation would have the following properties: it must not be capable of causing a chronic inflammatory response or foreign body reaction; it must not be immunogenic or carcinogenic over time; its physical properties (compressibility, stress resistance, compressive strength, etc.) must appropriately match the local tissue environment at the delivery site; it should be possible to contour the material to the desired shape for augmentation; it should be non-resorbable; it should be available in adequate quantities; it should not degrade in the body and should be sufficiently durable that it does not wear out or generate particles that could cause an inflammatory response over time; it should remain in position and should not migrate from the implantation site; it should not change in shape or volume over time; and it should be cost effective [2].

Injectable collagen has been used extensively for soft tissue augmentation [3–8,10–16]. It has been used for filling wrinkles, earlobe and lip augmentation, correction of scarring, treatment of glottic insufficiency, rehabilitating the vocal folds and larynx, correction of atrophies, correction of contour deficiencies, and the like.

However, when using collagen for soft tissue augmentation, overcorrection (i.e., injection of more material than just the amount needed to fill a defect) is needed due to rapid resorption of the liquid carrier which represents a large percentage of the injected volume [3,11,13]. Hypersensitivity, including erythema, induration and possibly pruritis, may also be a problem [4,10,12–15] and an association between collagen implants and autoimmune diseases such as dermatomyositis has been shown [7,10]. Granulomatous reactions to collagen implants have been observed [8], as have abscess formation and local necrosis [9,10]. Collagen injection to the vocal folds has resulted in chronic inflammation of the larynx [ 11 ]. In some cases, correction of atrophy using collagen injection has resulted in an unacceptable pustulous appearance [16]. In addition to the above, collagen is bioabsorbed in vivo and complete absorption usually occurs within 12 to 18 months. Such bioabsorption necessitates, of course, reinjection of additional collagen composition. Dunn, et al. [32] discloses other bioabsorbable polymer compositions for in vivo use which similarly suffer from the same deficiencies.

Textured dimethylsiloxane particles suspended in a hydrogel, such as Bioplastique™, have been injected for soft tissue augmentation [12,17–20]. The gel carrier is rapidly dispersed and a fibrotic capsule forms around the particles to create a stable implant [18]. However, this material is best used under, not in, the skin and therefore is not useful to correct wrinkles [12,19]. Also, problems may arise if the particles migrate before fibrosis is complete [17]. Overcorrection with this material may cause cord like subcutaneous indurations and the product remains palpable wherever it is injected [20]. This product may also cause a foreign body reaction in the host [21].

Other materials have been used for soft tissue augmentation. These include gelatin matrix implants, which have been used in patients hypersensitive to collagen [4,22]. These materials, however, may cause an immune response in the implanted patients.

Autologous fat injections have also been used, but produce only temporary results [12]. Paraffin has a long history of use in soft tissue augmentation, but often results in unacceptable deformaties [3]. Pastes comprising Teflon™ particles have also been used, but may migrate and/or cause inflammation [5,6]. Similarly, liquid and particulate silicones have been used in soft tissue augmentation [3,23].

Use of hydrogel polymer compositions such as those described by Stoy, et al. [31] have been proposed for use in soft tissue augmentation. Upon injection, these hydrogel compositions absorb water from the surrounding tissue and, accordingly, can cause osmotic shock and death to the cells in contact with the hydrogel.

In addition to the various problems associated with many of the substances used for soft tissue augmentation, the methods currently employed for delivering injectable materials to the tissue have certain disadvantages. In particular, the amount of material necessary for augmentation must typically be estimated based mostly on the skill and experience of the physician particularly when resorbable materials such as collagen and autologous fat are used. If an insufficient amount of material is injected in the first procedure or when resorption occurs, top-up injections administered in subsequent procedures are almost always necessary. Such subsequent injections, often as many as three to six, may not smoothly interface with the original injection, resulting in unsightly surface irregularities. Accordingly, it would be advantageous to be able to more accurately monitor the size of the occlusion formed by the injected material to ensure that it is sufficient to augment the tissue. Additionally, if follow-up injections are necessary, it would be advantageous to be able to locate accurately the site of the material previously injected. Further, compositions comprising materials such as Telfon and collagen have high viscosities and must be injected through large bore needles.

In view of the above, it is evident that there is an ongoing need in the art for new methods of soft tissue augmentation in mammals. Preferably, such methods would allow an occlusion-forming substance to be delivered accurately to the tissue. The substance employed would preferably conserve its volume in vivo, be non-migratory and be substantially non-immunogenic.

This invention is directed to the discovery that soft tissue augmentation can be accomplished in mammals by delivering sufficient amounts of a composition comprising a biocompatible polymer and a biocompatible solvent to the tissue under conditions such that a polymer precipitate forms in situ in the tissue. The polymeric compositions of this invention are non-biodegradable and, accordingly, do not substantially decrease in volume over time and the polymers employed in these compositions have a water equilibrium content of less than about 15% and, accordingly, do not hydrate, swell or cause osmotic shock. Moreover, the injection process provides for a coherent mass, not particulates, which mass is non-migratory.

When a contrast agent is included in the compositions employed in this invention, the contrast agent permits monitoring of the injection by conventional methods while it is taking place to ensure that it is being carried out properly and that proper placement is obtained. The contrast agent also allows monitoring post-injection by conventional methods to ensure correct placement of the mass months or even years after injection. Conventional monitoring methods include, by way of example, fluoroscopy, ultrasound, and in some cases visual detection.

SUMMARY OF THE INVENTION

This invention is directed to the discovery that unexpected and surprising results are achieved when soft tissue augmentation in mammals is performed using a composition comprising a biocompatible polymer having a water equilibrium content of less than about 15% and a biocompatible solvent. In particular, deficiencies associated with the prior art procedures are reduced by the invention. Such deficiencies include, for example, problems associated with migration of particulates over time, the biodegradation of the injected mass (e.g., collagen type materials) employed to augment the tissue of the mammal, development of an immune response or hypersensitivity to the material used for augmentation, osmotic shock associated with hydration of the hydrogel polymer, problems associated with the accurate delivery of such substances, and problems associated with post-delivery monitoring of the deposited materials.

Accordingly, in one of its method aspects, this invention is directed to a method for soft tissue augmentation in a mammal, which method comprises delivering a composition comprising a biocompatible polymer having a water equilibrium content of less than about 15% and a biocompatible solvent to the tissue of the mammal to be augmented, wherein said delivery is conducted under conditions such that a polymer precipitate forms in situ in the tissue at the delivery site in the mammal. The composition may comprise a contrast agent.

In another aspect, the invention provides a method for the delivery of a composition comprising a biocompatible polymer having a water equilibrium content of less than about 15% and a biocompatible solvent to the soft tissue of the mammal which tissue already has deposited therein an initial amount of this composition which method comprises visualizing the position of the deposited composition in the tissue; delivering a composition comprising a biocompatible polymer and a biocompatible solvent to the tissue of the mammal containing said deposited composition, wherein said delivery is conducted under conditions such that additional polymer precipitate forms in situ in the tissue thereby further augmenting the tissue at the delivery site in the mammal.

The methods of this invention are preferably practiced using a kit of parts comprising a first member which is a polymeric composition comprising a biocompatible polymer having a water equilibrium content of less than about 15% and a biocompatible solvent; and a second member which is a needle selected from the group consisting of a puncture needle, a spinal needle and a needle tipped catheter.

In the compositions employed herein, the biocompatible polymer having a water equilibrium content of less than about 15% is preferably an ethylene vinyl alcohol copolymer or a cellulose acetate polymer. In a particularly preferred embodiment, the biocompatible polymer is selected to be substantially non-immunogenic. The biocompatible solvent is preferably ethyl lactate or dimethylsulfoxide (DMSO).

DETAILED DESCRIPTION OF THE INVENTION

This invention is directed to methods for soft tissue augmentation in mammals, which methods comprise delivering a composition comprising a biocompatible polymer having a water equilibrium content of less than about 15% and a biocompatible solvent to the tissue of the mammal to be augmented.

Prior to discussing this invention in further detail, the following terms will first be defined:

The term "soft tissue augmentation" includes, but is not limited to, the following: dermal tissue augmentation; filling of lines, folds, wrinkles, minor facial depressions, cleft lips and the like, especially in the face and neck; correction of minor deformaties due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; filling of indentations in the soft tissue, dermal or subcutaneous, due to, e.g., overzealous liposuction or other trauma; filling of acne or traumatic scars and rhytids; filling of nasolabial lines, nasoglabellar lines and infraoral lines.

The term "biocompatible polymer" refers to polymers which have a water equilibrium content of less than about 15% and which, in the amounts employed, are non-toxic, non-peptidyl, chemically inert, and substantially non-immunogenic when used internally in the mammal and which are substantially insoluble in the tissue. The biocompatible polymers do not substantially decrease in volume over time and, since the polymer forms a solid inert mass, it does not migrate to distant organs within the body. Suitable biocompatible polymers include, by way of example, cellulose acetates [24–26] (including cellulose diacetate [27]), ethylene vinyl alcohol copolymers [28,29], polyalkyl ($C_1$–$C_6$) acrylates, acrylate copolymers, polyalkyl alkacrylates wherein the alkyl and the alk groups contain no more than 6 carbon atoms, and the like. Additional biocompatible polymers are disclosed in U.S. patent application Ser. No. 08/655,822 entitled "Novel Compositions for Use in Embolizing Blood Vessels" and U.S. patent application Ser. No. 09/109,041 entitled "Vascular Embolizing Compositions Comprising Ethyl Lactate and Methods for Their Use" which applications are incorporated herein by reference in their entirety. Further examples of biocompatible polymers are provided by Park, et al. [30]. Preferably, the biocompatible polymer is also non-inflammatory when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the artisan.

As noted above, the biocompatible polymers do not appreciably absorb water upon contact with the fluid of the tissue and typically will have an equilibrium water content of less than about 15% water and preferably less than about 10% water.

Particularly preferred biocompatible polymers include cellulose diacetate and ethylene vinyl alcohol copolymer. Cellulose diacetate polymers are either commercially available or can be prepared by art-recognized procedures. In a preferred embodiment, the number average molecular weight, as determined by gel permeation chromatography, of the cellulose diacetate composition is from about 25,000 to about 100,000; more preferably from about 50,000 to about 75,000; and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. Preferably, the cellulose diacetate is selected such that a solution of 6% w/v (weight/volume) in ethyl lactate or DMSO has a viscosity of 80 or less centipoise at 20° C. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not significantly alter the physical or solidifying properties of the composition. Such additional monomers include, by way of example only, maleic anhydride, styrene, propylene, acrylic acid, vinyl acetate, and the like. Ethylene vinyl alcohol copolymers are either commercially available or can be prepared by art-recognized procedures. Preferably, the ethylene vinyl alcohol copolymer composition is selected such that a solution of 8% w/v of the ethylene vinyl alcohol copolymer in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter or needle delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative solubility of the composition in the biocompatible solvent as well as the rate of precipitation of the copolymer in an aqueous solution (e.g., body fluids). In a particularly preferred embodiment, the copolymers employed herein comprise a mole percent of ethylene of from about 25 to about 60 and a mole percent of vinyl alcohol of from about 40 to about 75. More preferably, these copolymers comprise from about 40 to about 60 mole percent of vinyl alcohol and from about 60 to 40 mole percent of ethylene. These compositions provide for requisite precipitation rates suitable for soft tissue augmentation in mammals.

The term "contrast agent" refers to a biocompatible (non-toxic) radiopaque material capable of being monitored during injection into a mammalian subject by, for example, radiography or fluoroscopy. The contrast agent can be either water soluble or water insoluble. Examples of water soluble contrast agents include metrizamide, iopamidol, iothalamate sodium, iodomide sodium, and meglumine.

The term "water insoluble contrast agent" refers to a water insoluble (i.e., has a water solubility of less than 0.01 mg/mL at 20° C.), radiopaque material capable of being monitored during injection into a mammalian subject by, for example, radiography. Examples of water insoluble contrast agents include tantalum, tantalum oxide, tungsten, and barium sulfate, which are commercially available in the proper form for in vivo use. Other water insoluble contrast agents include gold, tungsten and platinum.

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethyl lactate, analogues/homologues/isomers of ethyl lactate, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with tissue fluids. Preferably, the biocompatible solvent is ethyl lactate or dimethylsulfoxide.

Compositions

The polymer compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer based on the total weight of the polymer composition and more preferably from about 4 to about 7.0 weight percent. If necessary, gentle heating and stirring can be used to effect dissolution of the biocompatible polymer into the biocompatible solvent, e.g., 12 hours at 50° C.

When a contrast agent is used, sufficient amounts of the contrast agent are then added to the solution to achieve the effective concentration for the complete polymer composition. Preferably, the polymer composition will comprise from about 10 to about 40 weight percent of the contrast agent and more preferably from about 20 to about 40 weight percent and even more preferably about 30 weight percent each based on the total weight of the polymer composition including the biocompatible polymer and the biocompatible solvent. When the contrast agent is not soluble in the biocompatible solvent, stirring is employed to effect homogeneity of the resulting suspension. In order to enhance formation of the suspension, the particle size of the contrast agent is preferably maintained at about 10 $\mu$m or less and more preferably at from about 1 to about 5 $\mu$m (e.g., an average size of about 2 $\mu$m).

The particular order of addition of components to the biocompatible solvent is not critical and stirring of the resulting composition is conducted as necessary to achieve homogeneity of the composition. Preferably, mixing/stirring of the composition is conducted under an anhydrous atmosphere (e.g., dry nitrogen or argon) at ambient pressure. The resulting composition may be heat sterilized and then stored preferably in sealed bottles (e.g., amber vials) until needed. Alternatively, if the composition is a true solution (i.e., not a suspension), sterilization of the composition can be achieved by aspectic filling procedures typically employing a small pore biofilter.

Each of the polymers recited herein is commercially available but can also be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Methods

The compositions described above are then employed in methods for soft tissue augmentation in mammals. In these methods, the composition is introduced to the tissue via conventional needle tip catheter or needle technology using, for example, techniques similar to those used to introduce collagen based soft tissue augmentation materials. Specifically, the injection may be performed through a puncture needle or spinal needle placed directly in the dermis or other tissue to be augmented. Alternatively, in certain situations, the tissue can be exposed surgically and the composition injected directly into the tissue.

Upon discharge of the composition from the catheter or the needle into the tissue, the biocompatible solvent dissipates into the fluid of the tissue resulting in the precipitation of the biocompatible polymer which precipitate forms a coherent mass. The formed precipitate in the tissue augments the tissue at the delivery site.

The particular amount of polymer composition employed is dictated by various factors such as the size of the correction to be made, the volume to be injected, the rate of precipitation (solids formation) of the polymer, etc. Such factors are well within the skill of the artisan.

The methods of this invention are particularly advantageous, when a contrast agent is used in the composition, it permits monitoring of the delivery of the biocompatible polymer while deposition is taking place either by fluoroscopy, ultrasound, or visually. In this way, one can ensure that the biocompatible polymer is being delivered to the optimal location in the tissue as well as determine whether the size of the polymer precipitate thus-formed will be sufficient to augment the tissue.

Moreover, the treatment process can be modified by altering the rate of precipitation of the polymer which can be controlled merely by changing the overall hydrophobicity/hydrophilicity of the polymer. As is understood in the art, faster precipitation rates are achieved by a more hydrophobic polymer composition.

When delivery of the polymeric composition to the tissue is conducted with a small diameter medical catheter (e.g., via a cytoscope), the catheter employed is not critical provided that polymeric catheter components are compatible with the polymeric composition (i.e., the catheter components will not readily degrade or leach in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the composition can be readily determined by the skilled artisan and include, for example, other polyolefins, fluoropolymers (e.g., polytetrafluoroethylene, perfluoroalkoxy resin, fluorinated ethylene propylene polymers), silicone, etc.

When introduced into the tissue, the biocompatible solvent rapidly diffuses into the fluids of this tissue leaving a solid precipitate. The precipitate is a coherent mass of the biocompatible polymer. Without being limited to any theory, it is believed that this precipitate augments the soft tissue.

Another advantage of this invention is that the precipitate forms a coherent mass which is substantially retained at the site of injection thereby obviating prior art concerns with migration of injected particulates. Moreover, the polymeric compositions of this invention are non-biodegradable and, accordingly, do not substantially decrease in volume over time.

Still another advantage of this invention is that the polymer employed can be selected to be non-immunogenic thereby obviating concerns raised by use of collagen-type materials which can produce an immune response in vivo.

Yet another advantage of this invention, in particular when a water insoluble contrast agent is used, is the formation of a polymeric mass in the tissue which may be monitored by the physician over time to assure proper retention of the mass in the tissue. Additionally, if a subsequent injection is necessary to further augment the soft tissue in the mammal, placement of the additional polymeric material is facilitated when the material previously implanted can be visualized by, for example, fluoroscopy, ultrasound, and the like. A subsequent injection can occur at any time after the initial injection including, for example, months or years later.

In view of the above, the methods of this invention are preferably practiced using a kit of parts which kit contains a first member which is a polymeric composition comprising a biocompatible polymer having a water equilibrium content of less than about 15% and a biocompatible solvent, and a second member which is a needle selected from the group consisting of a puncture needle, a spinal needle and a needle tipped catheter.

Utility

The methods described herein are useful in treating mammals requiring soft tissue augmentation. Accordingly, these methods find use in human and other mammalian subjects requiring such treatment. Soft tissue augmentation includes subcutaneous delivery, intradermal delivery and sub dermal delivery of the compositions described herein. In addition, delivery of the compositions to sphincter sites in vivo is contemplated including delivery to the esophageal sphincter, the anal sphincter, and the like. Sphincter delivery bulks the sphincter in a manner which permits coappation thereby retaining its sphincter function.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| cm = | centimeter |
| DMSO = | dimethylsulfoxide |
| EVOH = | ethylene vinyl alcohol copolymer |
| g = | gram |
| GPC = | gel permeation chromatography |
| HEPA = | high efficiency particulate air |
| min. = | minute |
| mL = | milliliter |
| mm = | millimeter |
| $M_w$ = | weight average molecular weight |
| μm = | micron |
| w/v = | weight to volume |

In the following examples, Examples 1–2 illustrate the preparation of polymer compositions useful in the methods described herein which polymer compositions comprise EVOH and cellulose acetate. Example 3 demonstrates the biocompatibility, non-migratory and bulking properties of an EVOH polymer in vivo.

Example 1

An EVOH polymer composition was prepared by combining 8 grams of EVOH (44 mole percent ethylene) ($M_w$ 108,000 GPC), 30 grams of tantalum having an average particle size of about 3 μm (narrow size distribution), and 100 mL of anhydrous DMSO. Heating at about 50° C. for about 12 hours was used to aid dissolution. The composition was mixed until homogeneous.

Tantalum having an average particle size of about 3 μm (narrow size distribution) was prepared by fractionation wherein tantalum, having an average particle size of less than about 20 μm, was added to ethanol (absolute) in a clean environment. Agitation of the resulting suspension was followed by settling for approximately 40 seconds to permit the larger particles to settle faster. Removal of the upper portion of the ethanol followed by separation of the liquid from the particles results in a reduction of the particle size which is confirmed under a microscope (Nikon Alphaphot™). The process was repeated, as necessary, until an average 3 μm particle size was reached.

Example 2

A composition comprising 7% (w/v) of cellulose diacetate in ethyl lactate with 30% (w/v) tantalum powder was prepared in a HEPA clean hood in a 20 cc screw cap bottle with Teflon cap liner as follows: 1.05 g of cellulose diacetate (U.S.P. grade—39% acetyl content) was added to 15 mL of ethyl lactate (Aldrich E3410-2), using a pipet for transfer. The bottle was briefly flushed with filtered, dry, prepurified nitrogen and capped. Exposure of ethyl lactate to air was minimized. The composition was shaken gently to dissolve. Then, 4.5 g of tantalum micronized powder (average particle size was 2 microns) was added to the bottle, which was flushed with nitrogen, capped and shaken gently for 1 min. Then, 2.5 cc aliquots were transferred into six 3.0 cc vials, flushed with nitrogen, capped and sterilized at 125° C. for 60 minutes.

Example 3

The purpose of this example is to demonstrate the biocompatibility of an EVOH polymer composition with the soft tissue of a mammal and to illustrate the non-migratory properties of such a polymer composition.

A 125 pound female sheep was anesthetized with an intramuscular injection of Ketamine and maintained on a respirator with oxygen ($O_2$)/halothane. The right inner thigh of the sheep was shaved and prepped with a Betadine scrub. A composition comprising ethylene vinyl alcohol prepared as in Example 1 above was shaken to disperse the tantalum contrast agent. Afterwards, about 0.8 cc of the composition was withdrawn into a 1 cc syringe fitted with a 26 gage needle. The shaved skin of the thigh was punctured with the needle and about 0.25 cc of the composition was injected intradermally. A visible bleb or dome (12 mm in width×2 mm in height) formed at the injection site. About 3 cm beneath this site another 0.25 cc of the composition was injected subdermally, with similar results.

The animal was then awakened from the anesthesia with no ill effects. The two raised skin sites from the injections were unchanged after 4 hours. The animal was examined at 48 hours post-injection. There was some reddening observed around the two injection sites, which resolved within one week. The animal was sacrificed four (4) weeks later and the tissue adjacent the injection sites wa examined which examination revealed no inflammation (i.e., reddening or swelling of the tissue) nor migration of the solid mass from the site of the injection.

From the foregoing description, various modifications and changes in the composition and method will occur to those skilled in the art. All such modifications coming within the scope of the appended claims are intended to be included therein.

What is claimed is:

1. A method for extra-vascular soft tissue augmentation in a mammal, which method comprises extra-vascularly delivering a composition to the tissue to be augmented, said composition comprising a biocomptible polymer having a water equilibrium content of less than about 15% and a biocompatible solvent, wherein the extra-vascular delivery is conducted under conditions such that a nonbiodegradable polymer precipitate forms in situ in the extra-vascular soft tissue thereby augmenting the tissue at the delivery site and the delivery is selected from the group consisting of subcutaneous delivery, intradermal delivery and subdermal delivery.

2. The method according to claim 1 wherein said biocompatible polymer is selected from the group consisting of cellulose acetate polymers, ethylene vinyl alcohol copolymers and polyacrylates.

3. The method according to claim 2 wherein said biocompatible polymer is a cellulose acetate polymer or an ethylene vinyl alcohol copolymer.

4. The method according to claim 1 wherein said biocompatible solvent is selected from the group consisting of dimethylsulfoxide, ethanol, ethyl lactate, and acetone.

5. The method according to claim 4 wherein said biocompatible solvent is dimethylsulfoxide.

6. The method according to claim 1 wherein the composition further comprises a contrast agent.

7. The method according to claim 6 wherein said contrast agent is a water insoluble contrast agent.

8. The method according to claim 7 wherein said water insoluble contrast agent is selected from the group consisting of tantalum, tantalum oxide, tungsten, and barium sulfate.

9. The method according to claim 6 wherein said contrast agent is a water soluble contrast agent.

10. The method according to claim 1 wherein said composition is delivered into the soft tissue via a needle and syringe.

11. A method for the extra-vascular delivery of a composition comprising a biocompatible polymer having a water equilibrium content of less than about 15% and a biocompatible solvent to the extra-vascular soft tissue of a mammal which tissue already has deposited therein an initial amount of this composition, which method comprises visualizing the position of the deposited composition in the extra-vascular tissue and extra-vascularly delivering a composition comprising a biocompatible polymer having a water equilibrium content of less than about 15% and a biocompatible solvent to the tissue containing said deposited composition, wherein the delivery is selected from the group consisting of subcutaneous delivery, intradermal delivery and subdermal delivery and is conducted under conditions such that a nonbiodegradable polymer precipitate forms in situ in the tissue thereby further augmenting the tissue at the delivery site.

12. The method according to claim 11 wherein the initial deposit was made during a prior procedure.

13. The method according to claim 11 wherein visualization is conducted by direct visualization, fluoroscopy or ultrasound.

14. The method according to claim 11 wherein the composition further comprises a contrast agent.

* * * * *